(12) United States Patent
Kim et al.

(10) Patent No.: US 11,660,068 B2
(45) Date of Patent: May 30, 2023

(54) MEDICAL HEADGEAR AND TRANSCRANIAL ULTRASOUND TRANSMISSION DEVICE COMPRISING THE SAME

(71) Applicant: NEUROSONA CO., LTD., Seoul (KR)

(72) Inventors: Ji Yeun Kim, Seoul (KR); Jeong Hyeon Park, Seoul (KR); Seoung Won Shin, Gyeonggi-do (KR); Seung Schik Yoo, Seoul (KR)

(73) Assignee: NEUROSONA CO., LTD., Seoul (KR)

( * ) Notice: Subject to any disclaimer, the term of this patent is extended or adjusted under 35 U.S.C. 154(b) by 808 days.

(21) Appl. No.: 16/567,182

(22) Filed: Sep. 11, 2019

(65) Prior Publication Data
US 2020/0000428 A1 Jan. 2, 2020

Related U.S. Application Data (63) Continuation of application No. PCT/KR2018/002578, filed on Mar. 5, 2018.

(30) Foreign Application Priority Data

Mar. 16, 2017 (KR) .................. 10-2017-0033208
May 26, 2017 (KR) .................. 10-2017-0065629

(51) Int. Cl.
*A61B 8/00* (2006.01)
*A61B 8/08* (2006.01)
(Continued)

(52) U.S. Cl.
CPC .......... *A61B 8/4209* (2013.01); *A61B 8/0808* (2013.01); *A61B 90/50* (2016.02);
(Continued)

(58) Field of Classification Search
CPC ... A61B 8/4209; A61B 8/0808; A61B 8/4218; A61B 8/4245; A61B 8/4281;
(Continued)

(56) References Cited

U.S. PATENT DOCUMENTS 5,954,642 A * 9/1999 Johnson ............. G02B 27/0176 600/300
6,669,635 B2 12/2003 Kessman et al.
(Continued)

FOREIGN PATENT DOCUMENTS

DE 202015002204 6/2015
DE 202015002204 U1 * 7/2015 ............. A61B 90/50
(Continued)

OTHER PUBLICATIONS

International Search Report and Written Opinion for Application No. PCT/KR2018/002578 dated Jun. 4, 2018, 12 pages.
(Continued)

*Primary Examiner* — Sean D Mattson
(74) *Attorney, Agent, or Firm* — Miyoung Shin; Guntin & Gust, PLC (57) ABSTRACT

A medical headgear includes an ultrasound transducer and a headgear. The ultrasound transducer is configured to generate a low intensity ultrasound. The headgear supports the ultrasound transducer. The headgear includes a rear portion case including a slide guide configured to support an occipital and a support pad configured to support a crown. The headgear further includes a front portion case connected to the rear portion case to be slidably movable in one direction. The front portion case includes two temporal support pads configured to support both temporal portions.

16 Claims, 9 Drawing Sheets

(51) Int. Cl.
    *A61N 7/00*     (2006.01)
    *A61B 90/50*     (2016.01)
    *A61B 90/14*     (2016.01)
    *A61B 5/00*     (2006.01)
    *A61N 2/00*     (2006.01)
    *A61B 90/00*     (2016.01)

(52) U.S. Cl.
    CPC .............. *A61N 7/00* (2013.01); *A61B 5/6814* (2013.01); *A61B 8/4218* (2013.01); *A61B 8/4245* (2013.01); *A61B 8/4281* (2013.01); *A61B 90/14* (2016.02); *A61B 2090/3979* (2016.02); *A61B 2090/502* (2016.02); *A61N 2/006* (2013.01); *A61N 2007/0026* (2013.01)

(58) Field of Classification Search
    CPC ..... A61B 8/4444; A61B 8/4477; A61B 90/50; A61B 90/14; A61B 5/6814; A61B 2090/3979; A61B 2090/502; A61B 2090/374; A61B 2090/3762; A61B 2090/3937; A61B 2090/397; A61B 2576/023; A61N 7/00; A61N 2/006; A61N 2007/0026
    See application file for complete search history.

(56) References Cited

U.S. PATENT DOCUMENTS

| | | | | |
|---|---|---|---|---|
| 2007/0167765 | A1* | 7/2007 | Unger | A61B 8/481 600/437 |
| 2012/0083717 | A1* | 4/2012 | Alleman | A61B 8/546 601/2 |
| 2015/0112153 | A1 | 4/2015 | Nahum | |
| 2017/0065835 | A1* | 3/2017 | Park | A61B 6/501 |
| 2017/0296295 | A1* | 10/2017 | Wagner | A61N 7/00 |
| 2017/0333724 | A1* | 11/2017 | Lee | A61B 90/50 |
| 2018/0132746 | A1* | 5/2018 | Imajo | A61B 5/369 |
| 2018/0177491 | A1* | 6/2018 | Hynynen | A61B 34/10 |

FOREIGN PATENT DOCUMENTS

| | | | | |
|---|---|---|---|---|
| JP | 2006-305047 | A | 11/2006 | |
| JP | 2012-081152 | | 4/2012 | |
| JP | 2016-214608 | | 12/2016 | |
| JP | 2016-214608 | A | 12/2016 | |
| KR | 10-2012-0059232 | A | 6/2012 | |
| KR | 10-2015-0055613 | A | 5/2015 | |
| KR | 10-2015-0102470 | A | 9/2015 | |
| WO | 2015073903 | | 5/2015 | |
| WO | WO-2015075603 | A1 * | 5/2015 | ........... A61B 8/0808 |
| WO | 2016069178 | | 5/2016 | |
| WO | 2016185707 | | 11/2016 | |

OTHER PUBLICATIONS

Extended European Search Report issued in corresponding EP application 18767978, dated Nov. 18, 2020.
Muller, M.D., et al., Letter to the Editor, A Probe-Holder for Bilateral Transcranial Doppler Sonography, Ultrasound in Medicine & Biology, pp. 105-108, vol. 18(1), 1992, Pergamon Press plc.
Office Action issued in Corresponding JP Patent Application No. 2019-572330, dated Aug. 18, 2020.

* cited by examiner

MEDICAL HEADGEAR AND TRANSCRANIAL ULTRASOUND TRANSMISSION DEVICE COMPRISING THE SAME

RELATED APPLICATIONS

This Application is a continuation of PCT Application No. PCT/KR2018/002578 filed Mar. 5, 2018 and claiming priority to Korean Patent Application Nos. 10-2017-0033208 filed Mar. 16, 2017 and 10-2017-0065629 filed May 26, 2017, disclosures of which are incorporated herein in their entirety.

TECHNICAL FIELD

The present disclosure relates to a medical headgear and a transcranial ultrasound transmission device including the same, and more particularly, to a medical headgear supporting an ultrasound transducer capable of transmitting low intensity ultrasound to transcranial and a transcranial ultrasound transmission device including the same.

BACKGROUND ART

Brain function is expressed in human cognition and behavior by transmitting signals through a white cortex through activation and deactivation of cell groups distributed in the brain and having specific roles and their biological tissues. To control the brain function, first, there is a method of adjusting a degree to which neurotransmitters are activated in brain cells through drugs. However, it is impossible to control only a desired specific site using a drug. On the other hand, an electrical stimulation using a probe, which is a method of controlling the brain function through an invasive method is possible. In the case of electrical stimulation using such a probe, electrocorticogram or deep brain stimulation (DBS) used in a brain operation makes it possible to transplant or insert the probe into a specific position in the brain and apply the electrical stimulation to temporarily or permanently change the brain function. A similar device is a transcranial magnetic stimulation (TMS) device, which is a technique for controlling the brain function in a noninvasive manner from the outside. This is a method of adjusting the brain function by generating a strong magnetic field outside the skull to induce an induced current in a brain cortex. Such a TMS device has a problem in that a precise control is difficult because not only a non-invasively stimulated area of the brain cortex is too large (2 cm 3 cm or more) but also stimulation is possible only in the skull and a surface of the brain cortex of a depth of 1 cm~cm and the magnitude of the magnetic field is drastically reduced in an area located deeper in the brain.

A device using ultrasound is proposed to solve the above problem. Ultrasound may penetrate the skull upon illumination at a frequency of less than 1 MHz, which is lower than a high frequency used in diagnostic ultrasound devices in a pressure impact waveform and may focus on a deep area of the brain, unlike TMS. Furthermore, it is possible to control a detailed function of a specific brain area because a sphere or an elliptical cone-shaped sphere (a rice grain shape) having a size of 2 mm to 3 mm is affected by ultrasound.

An ultrasound transducer for generating ultrasound needs to be closely attached to and supported by the skull of a human body so as to transmit ultrasound to transcranial. The skull of the human body may be formed in various sizes and shapes according to race, age and sex, and an affected part, that is, a position of the brain, to which ultrasound needs to be transmitted, may also vary. Therefore, a user, for example, medical staff, has a problem in constantly adhering and supporting the ultrasound transducer according to the shape and size of the skull and the position of the brain to which ultrasound needs to be transmitted.

SUMMARY

Technical Problem

Provided are a medical headgear capable of being mounted on a skull of an object while supporting an ultrasound transducer, and a transcranial ultrasound transmission device including the same.

Provided is a medical headgear capable of closely adhering and supporting an ultrasound transducer to a skull of an object regardless of the size and shape of a skull of the object and a position of the brain to which ultrasound needs to be transmitted, and a transcranial ultrasound transmission device including the same.

Solution to Problem

According to an aspect of the present disclosure, a medical headgear includes an ultrasound transducer configured to generate a low intensity ultrasound; and a headgear by which the ultrasound transducer is supported, wherein the headgear includes a rear portion case comprising an occipital portion support unit configured to support an occipital and a crown support unit configured to support a crown; and a front portion case connected to the rear portion case to be slidably movable in one direction and comprising two temporal portion support units configured to support both temporal portions.

The front portion case may include a front portion band extending in one direction and having the two temporal portion support units disposed at both ends, respectively; and a slide band extending in one direction between the crown support unit and the front portion band.

One end of the slide band may be fixed to the front portion band and another end is slidably supported on an occipital portion case.

In a first operation mode in which an operation is performed on a frontal lobe, the slide band may slide in a first direction toward the crown support unit, and in a second operation mode in which an operation is performed on a temporal lobe, the slide band may slide so as to be spaced apart from the crown support unit in a second direction opposite to the first direction.

The medical headgear may further include a slide locking device configured to fix a position of the slide band according to the first and second operation modes.

The front portion band may be provided with an elastic member deformable along a head circumference of the object.

The medical headgear may further include a first marker supported by the occipital portion case and comprising at least one infrared reflector configured to sense a position of the headgear.

The medical headgear may further include a first lower face support unit extending in one direction and having both ends supported on both ends of the rear portion case respectively to support a lower face of the object.

The medical headgear may further include a second lower face support unit extending in one direction and having both ends supported on both ends of the front portion band respectively to support a lower face of the object.

The ultrasound transducer may include an ultrasound generating device configured to generate the low intensity ultrasound and an applicator configured to fix the ultrasound generating device to a scalp of the object.

The medical headgear may further include a second marker supported by the ultrasound transducer and comprising one or more infrared reflectors configured to sense a focal direction of the ultrasound generating device.

The medical headgear may further include a connecting device disposed between the headgear and the ultrasound transducer to connect the headgear to the ultrasound transducer.

The connecting device may include a plurality of link structures.

The connecting device may include a first connecting bar and a second connecting bar disposed between the headgear and the ultrasound transducer, a first joint configured to connect the headgear to the first connecting bar, a second joint configured to connect the first connecting bar to the second connecting bar, and a third joint configured to connect the second joint to the ultrasound transducer.

The medical headgear may further include a link restraining device disposed in the second joint to restrain the first joint to the third joint.

The occipital portion support unit may extend in a circumferential direction of the occipital region, and may further include an occipital portion regulating unit extending or contracting the occipital portion support unit.

A transcranial ultrasound transmission device according to an embodiment of the present disclosure may include the medical headgear according to an embodiment.

Advantageous Effects of Disclosure

According to the medical headgear according to an embodiment of the present disclosure, an ultrasound transducer supported on the headgear may be moved to a specific position of a skull regardless of a position of the brain to which ultrasound needs to be transmitted, and thus the use convenience of a user may be improved.

In addition, the medical headgear according to an embodiment of the present disclosure may be supported at three or more places of an object, and thus the positional restraining force between the skull and the headgear may be improved and the supporting force of the ultrasound transducer with respect to the object may be improved.

DETAILED DESCRIPTIONS OF EMBODIMENTS

The principle of the present disclosure is explained and embodiments are disclosed so that the scope of the present disclosure is clarified and one of ordinary skill in the art to which the present disclosure pertains implements the present disclosure. The disclosed embodiments may have various forms.

Throughout the specification, like reference numerals or characters refer to like elements. In the present specification, all elements of embodiments are not explained, but general matters in the technical field of the present disclosure or redundant matters between embodiments will not be described. Terms 'part' or 'portion' used herein may be implemented using software or hardware, and, according to embodiments, a plurality of 'parts' or 'portions' may be implemented in a single unit or element or a single 'part' or 'portion' may include a plurality of units or elements. The operational principle of the present disclosure and embodiments thereof will now be described more fully with reference to the accompanying drawings.

In the present specification, an image may include a medical image obtained by a medical imaging device, such as a computed tomography (CT) device, a magnetic resonance imaging (MRI) device, an ultrasound imaging device, or an X-ray device.

Throughout the specification, the term 'object' is a thing to be imaged, and may include a human, an animal, or a part of a human or animal. For example, the object may include a part of a body (i.e., an organ), a phantom, or the like.

The term "ultrasound image" in the entire specification refers to an image of an object that is transmitted to the object and processed based on an ultrasound signal reflected from the object.

Hereinafter, embodiments will be described in detail with reference to the drawings.

Figure 1A:
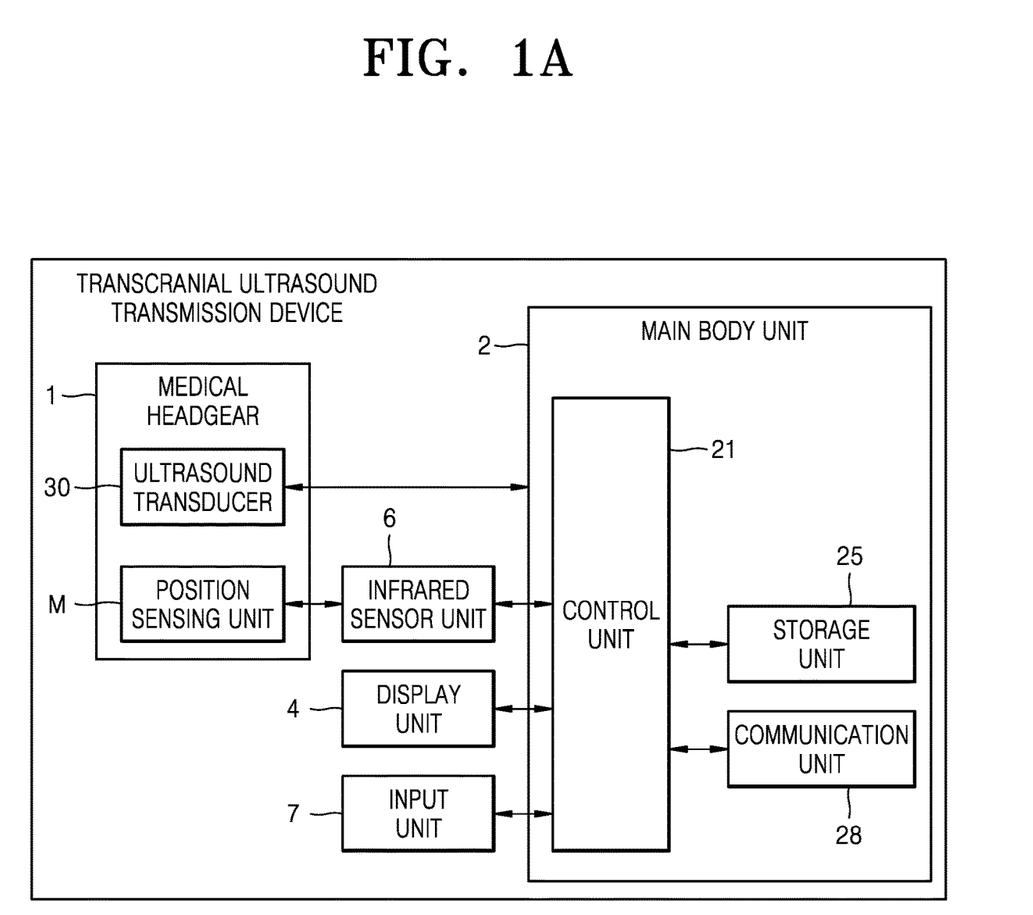
FIG. 1A is a block diagram of a transcranial ultrasound transmission device according to an embodiment of the present ultrasound.
Figure 1B:
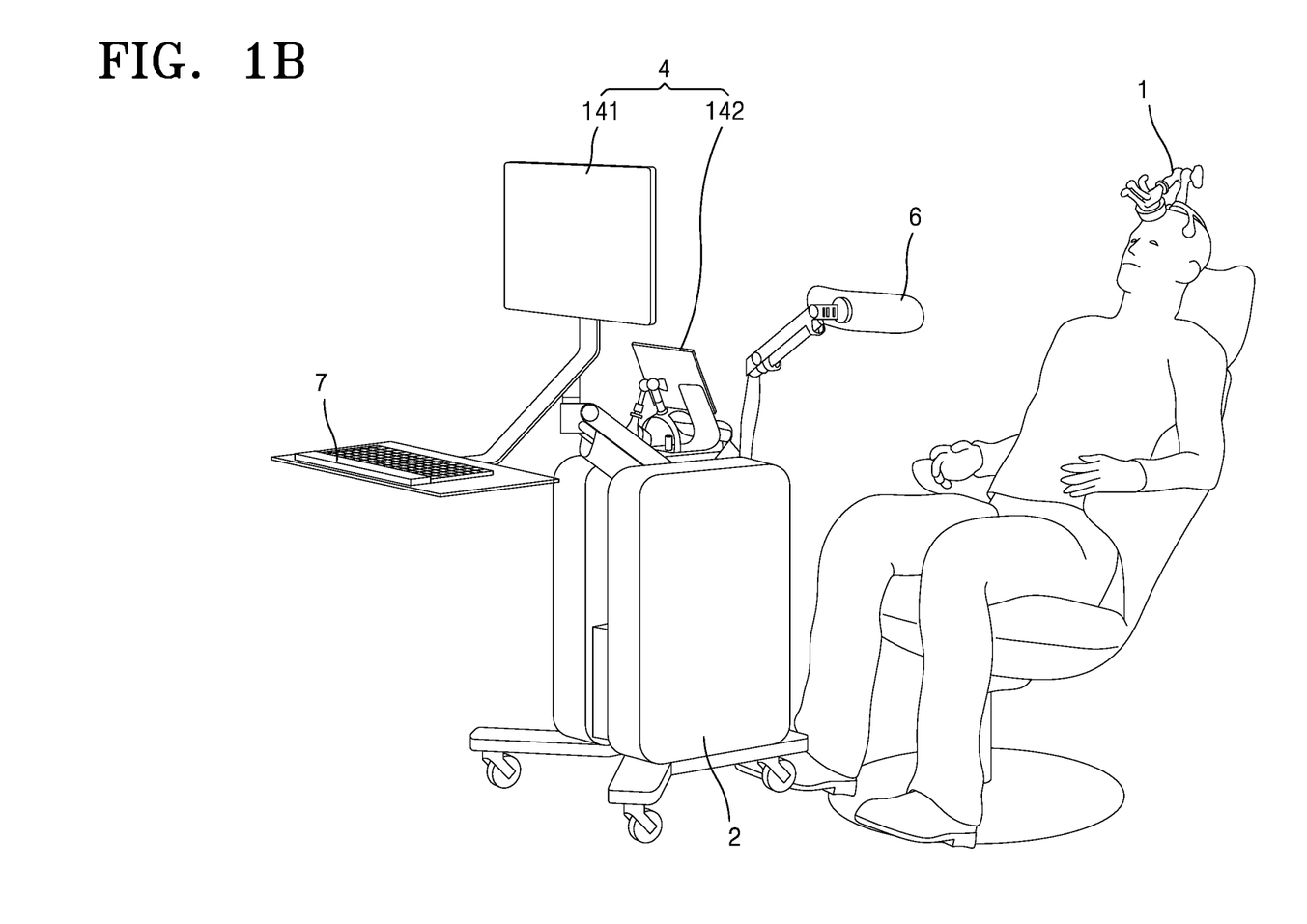
FIG. 1B is a perspective view of a transcranial ultrasound transmission device according to an embodiment of the present ultrasound.

FIG. 1A is a block diagram of a transcranial ultrasound transmission device according to an embodiment of the present ultrasound. FIG. 1B is a perspective view of a transcranial ultrasound transmission device according to an embodiment of the present ultrasound. The transcranial ultrasound transmission device according to an embodiment may include a medical headgear 1, a main body unit 2, a display unit 4, an infrared sensor unit 6, and an input unit 7.

The transcranial ultrasound transmission device may be implemented not only in cart form but also in portable form. Examples of the portable ultrasound transmission device may include, but are not limited to, a smart phone including the medical headgear 1 and an application, a laptop computer, a PDA, a tablet PC, and the like.

The medical headgear 1, which is a surgical device capable of transmitting ultrasound to an object while the object is wearing a headgear 10 (see FIG. 2), may include the headgear 10 supported on the head of the object, an ultrasound transducer 30 for transmitting ultrasound to the object, and a position sensing unit M capable of sensing positions of the ultrasound transducer 30 and the headgear 10 by interacting with the infrared sensor unit 6. As an example, the medical headgear 1 may be implemented as a separate type which is connected to the main body unit 2 by wire or wirelessly. Specific details related to the configuration of the medical headgear 1 will be described later in detail with reference to FIGS. 2 to 3.

The main body unit 2 may control the overall operation of the transcranial ultrasound transmission device and a signal flow between the internal components of the transcranial ultrasound transmission device. The main body unit 2 may include a control unit 21 for processing programs or data, a storage unit 25 for storing programs or data for performing functions of the transcranial ultrasound transmission device, and a communication unit 28 for connecting the control unit 21 to the medical headgear 1.

As an example, the control unit 21 included in the main body unit 2 may control the overall operation of the transcranial ultrasound transmission device and the signal flow between the internal components of the transcranial ultrasound transmission device. For example, the control unit 21 may control a transmission unit to form a transmission signal to be applied to each of a plurality of transducers included in the ultrasound transducer 30, taking into consideration positions and focusing points of the plurality of transducers or may control the operation of the transcranial ultrasound transmission device by receiving a control signal from the input unit 7 that will be described later or an external device.

The storage unit 25 may store various data or programs for driving and controlling the transcranial ultrasound transmission device. As an example, because a program for controlling the medical headgear 1 may be installed in the storage unit 25, the program may include an instruction to perform some or all of operations of the control unit 21. The program may be installed in advance in the storage unit 25 or a user may download a program from a server providing an application and install the program. The server providing the application may include a recording medium storing the program.

The communication unit 28 that is a communication device for connecting the medical headgear 1 to the main body unit 2 may include one or more components that enable communication between the medical headgear 1 and the main body unit 2. As an example, the communication unit 28 may include at least one of a near distance communication module, a wired communication module, and a wireless communication module. According to an example, the communication unit 28 may receive the control signal and the data and transmit the received control signal to the control unit 21 such that the control unit 21 controls the medical headgear 1 according to the received control signal.

The display unit 4 may display a generated ultrasound image and various types of information processed by the transcranial ultrasound transmission device. The display unit 4 may include one or a plurality of main display units 141 and a sub-display unit 142 according to an implementation type. One of the main display unit 141 and the sub-display unit 142 may be implemented as a touch screen. The main display unit 141 and the sub-display unit 142 may display the various types of information processed by the transcranial ultrasound transmission device. In addition, the main display unit 141 and the sub-display unit 142 may be implemented as the touch screen and provide a GUI, thereby receiving data for controlling the transcranial ultrasound transmission device from the user. For example, the main display unit 141 may display a control panel for controlling a display of the ultrasound image in a GUI form, and the sub-display unit 142 may display an operation status on an object. The main display unit 141 may receive data for controlling display of an image through the control panel displayed in the GUI form.

The infrared sensor unit 6 may sense the position of the medical headgear 1 worn by the object and a focus position of ultrasound transmitted by the ultrasound transducer 30 through infrared transmission and reception with the position sensing unit M disposed on the medical headgear 1. As an example, the position sensing unit M may include a first marker 115 (see FIG. 2) fixed to the headgear 10 and a second marker 33 (see FIG. 2) fixed to the ultrasound transducer 30. The infrared sensor unit 6 according to an embodiment may sense the position of the medical headgear 1, more specifically, a position of the object wearing the medical headgear 1, through an infrared transmission and reception process in relation to the first marker 115 fixed to the headgear 10. The infrared sensor unit 6 may also sense a focus direction and a focus position of the ultrasound in relation to the second marker 33 fixed to the ultrasound transducer 30.

The input unit 7 may receive an input of the user for controlling the transcranial ultrasound transmission device. For example, an input of the user may include an input for operating a button, a keypad, a mouse, a trackball, a jog switch, a knob, etc., an input for touching a touch pad or a touch screen, a voice input, a motion input, a bio information input (e.g., iris recognition, fingerprint recognition, etc.), and the like, but is not limited thereto.

Figure 2:
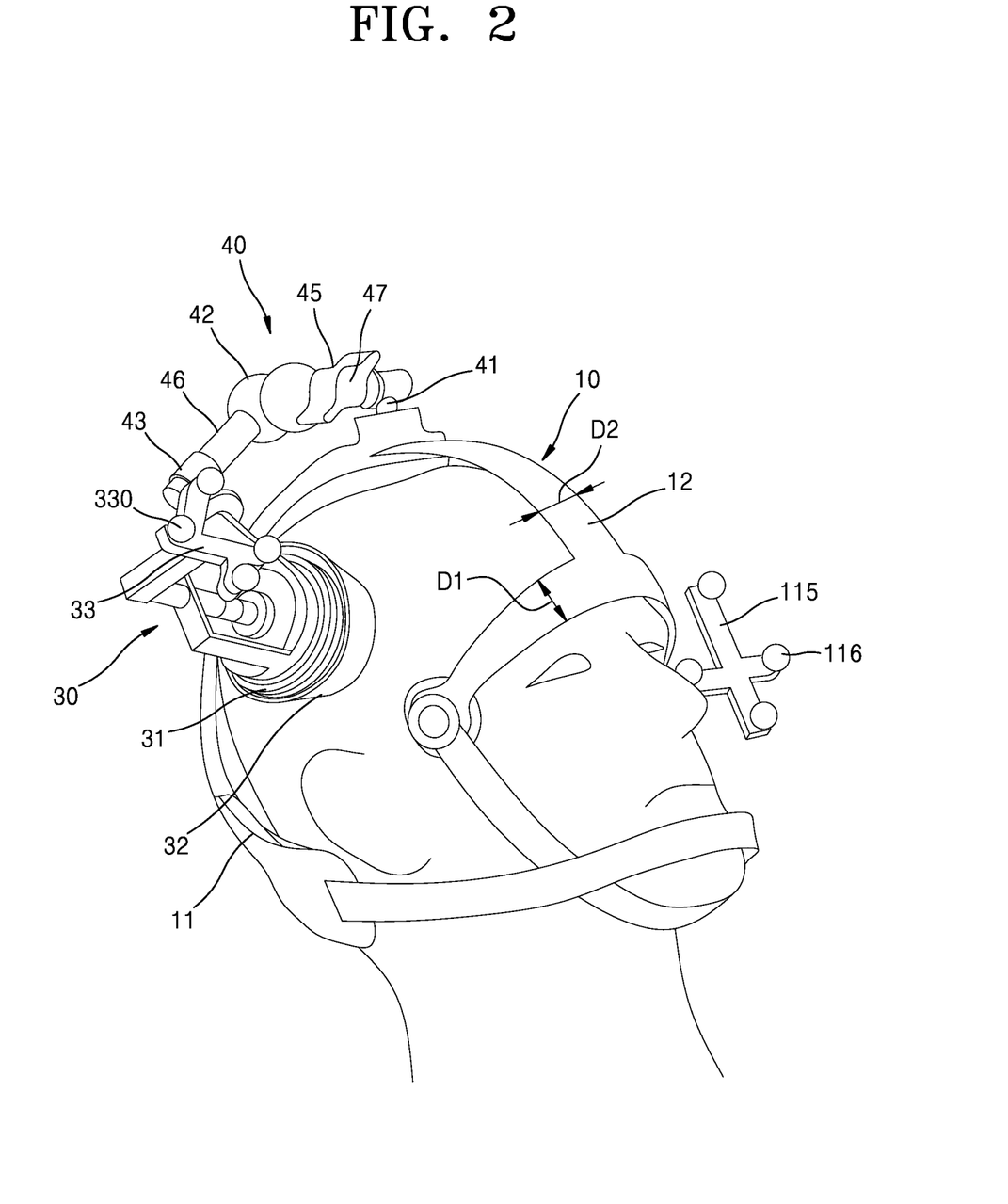
FIG. 2 is a perspective view of a medical headgear according to an embodiment of the present disclosure.
Figure 3A:
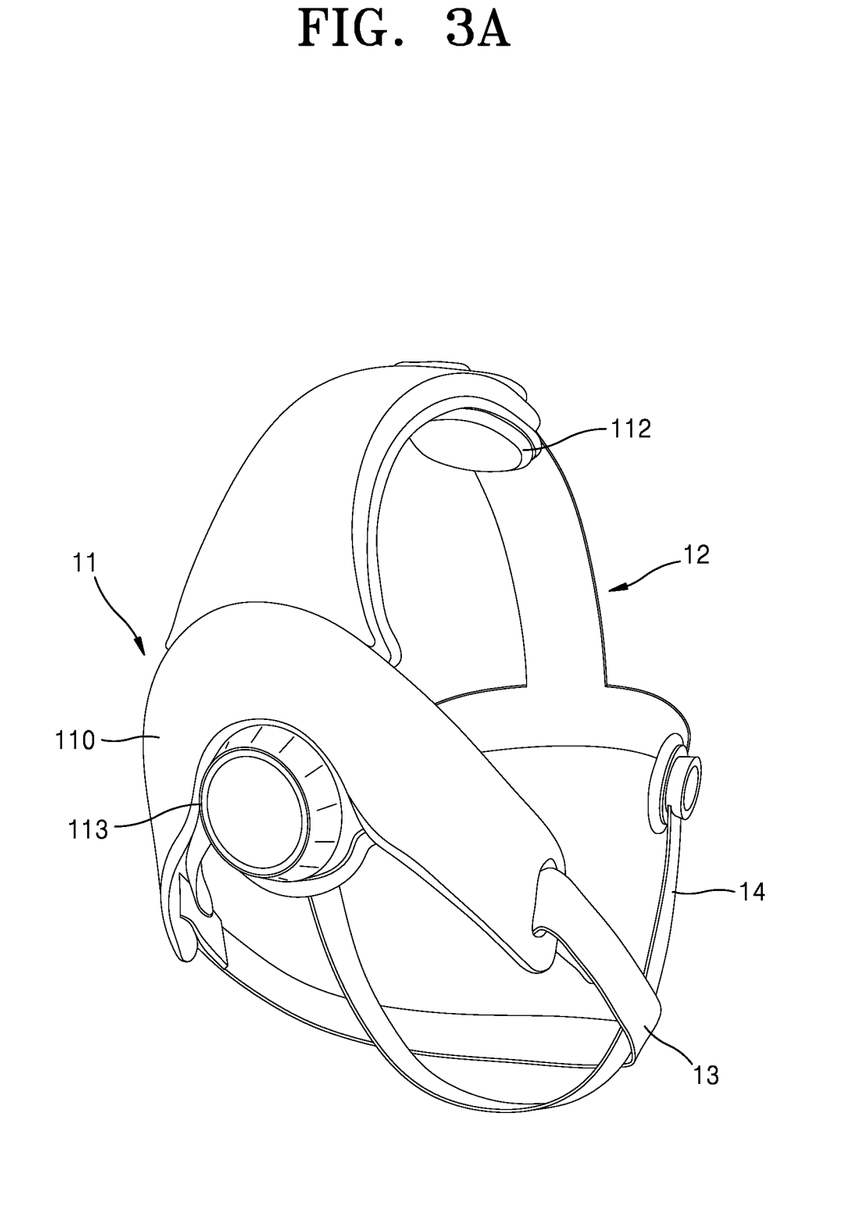
FIGS. 3A and 3B are perspective views of a headgear according to an embodiment of the present disclosure.
Figure 3B:
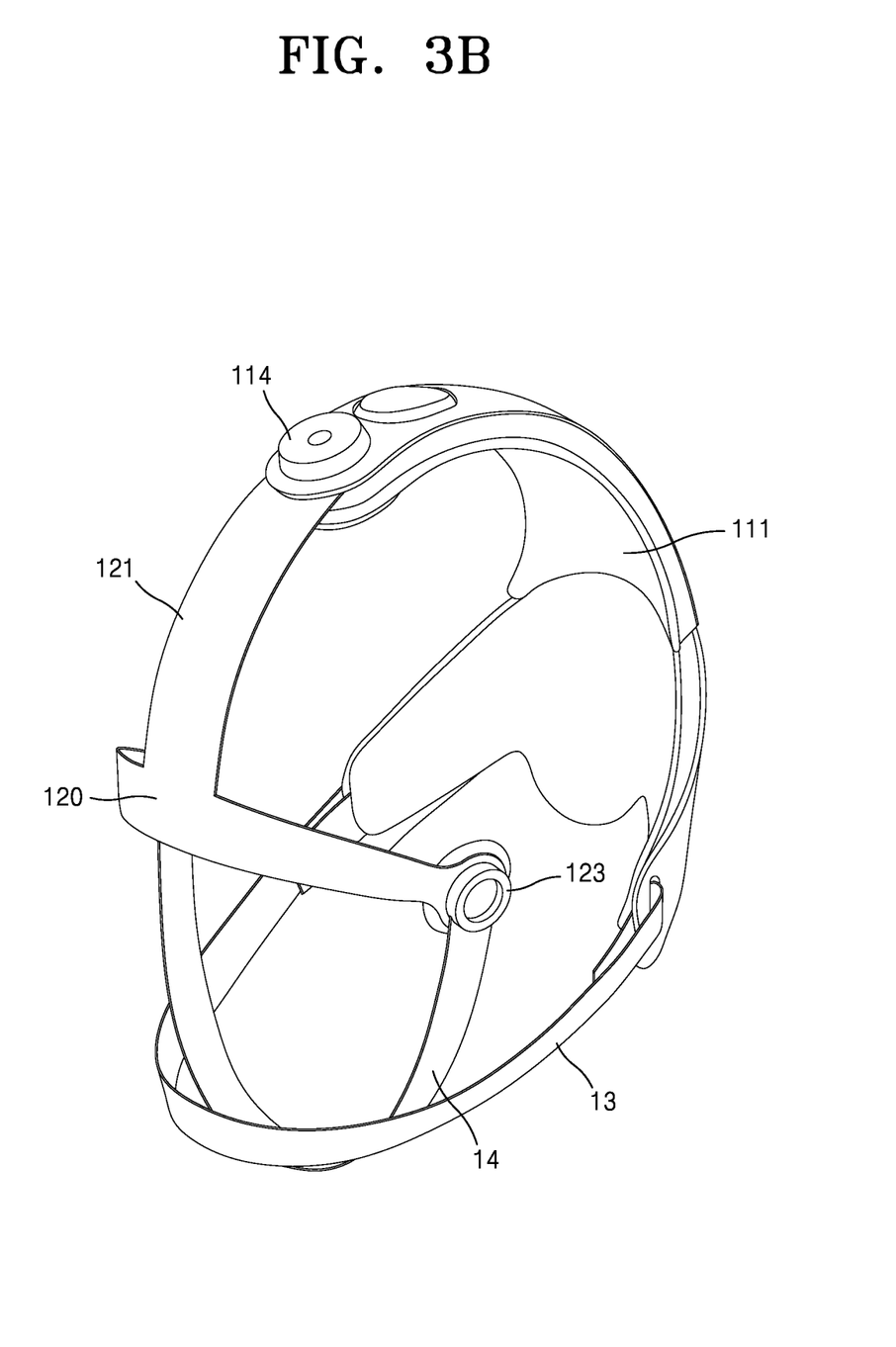

FIG. 2 is a perspective view of the medical headgear 1 according to an embodiment of the present disclosure. FIGS. 3A and 3B are perspective views of the medical headgear 1 according to an embodiment of the present disclosure. In the present disclosure, the medical headgear 1 means any of general protective articles to be worn on or supported by the head of an object. The medical headgear 1, according to an embodiment of the present disclosure, which is a support member worn on the head of the object and supported to be fixed to the head of the object, may include the headgear 10 supported by the head of the object, the ultrasound transducer 30, and a connecting device 40 for connecting the headgear 10 to the ultrasound transducer 30 together with the position sensing unit M.

Referring to FIGS. 2 to 3B, the headgear 10 according to an embodiment may include a rear portion case 11 disposed at a rear portion and supporting the head of the object, a front portion case 12 supported by a temporal portion of the head of the object, a first lower face support unit 13 and a second lower face support unit 14. As an example, the rear portion case 11, which is a support member supported on an occipital and a crown of the head of the object, may include an occipital portion support unit 110, an occipital portion pad 111, a crown support unit 112, and a first marker 115. The occipital portion support unit 110 is a support member capable of tightening or relaxing an occipital side by adjusting a length. At this time, the occipital portion support unit 110 may function as a first support point capable of directly supporting the occipital portion of the object. Further, as an example, the occipital portion support unit 110 may extend in a circumferential direction of the occipital portion of the object and may extend to cover the crown portion of the object. At this time, the occipital portion support unit 110 may be extended or contracted by an operation of an occipital portion regulating unit 113, thereby tightening or relaxing the occipital side of the object. For example, the occipital portion regulating unit 113 may be provided in adjustable dial form and may be an adjustable member capable of extending or contracting the occipital portion support unit 110 according to a rotational direction of the occipital portion regulating unit 113. As described above, by applying the occipital portion regulating unit 113 to the occipital portion support unit 110, even when a head size of the object, such as a diameter of the head, varies according to race, sex, age, etc., an operator may have the medical headgear 1 worn on the object by a simple operation of the occipital portion regulating unit 113.

The occipital portion pad 111 is a protecting and buffering member capable of improving the wearing comfort of the object together with the occipital portion regulating unit 113 described above. As an example, the occipital portion pad 111 may be disposed to face the occipital portion support unit 110 and be supported on the occipital portion support unit 110. At this time, the occipital portion pad 111 may be disposed inside the occipital portion support unit 110, that is, between the occipital portion of the object and the occipital portion support unit 110, and thus may be directly supported on the occipital portion of the object.

The crown support unit 112 is a support member disposed to face the crown of the object and support the crown of the object. As an example, the crown support unit 112 may be fixed to the occipital portion support unit 110 to serve as a second support point for directly supporting the crown of the object. In addition, the crown support unit 112 according to an embodiment may be implemented in pad form to perform a function as a protecting and buffering member to improve the wearing comfort of the object.

The first marker 115 is a position sensing unit arranged to determine, in real time, a position of the head of the headgear 10, more specifically, the head of the object wearing the headgear 10 when capturing an MRI image or a CT image. As an example, the first marker 115 may be arranged to be supported in the rear portion case 11, more specifically in the occipital portion support unit 110. At this time, the first marker 115 may be attached to the occipital portion support unit 110 in a detachable manner using a magnetic material. In addition, the first marker 115 may include one or more round bar-shaped infrared reflectors 116 that track a position of the occipital portion support unit 110. As an example, the infrared reflectors 116 may be implemented in four and disposed at four ends of a cruciform support unit, respectively.

As an example, the front portion case 12, which is a support member supported by the temporal portion of the head of the object, may include a front portion band 120, a slide band 121, and temporal portion support units 123. The front portion band 120 is a support member capable of supporting the temporal portion of the object. As an example, the front portion band 120 may be formed in a band shape extending in one direction, for example, extending from one temporal portion of the head to the other temporal portion in the circumferential direction of the head of the object. At this time, a width D1 of the front portion band 120 may be 1 cm or more and 10 cm or less. Also, at this time, both ends of the front portion band 120 may be disposed to face the temporal portion of the object and function as a third support point and a fourth support point. Also, as an example, the front portion band 120 may be provided in a deformable resilient member such that both ends of the front portion band 120 may be further proximate or spaced within a restoration range. Therefore, even when the head size of the object, for example, the diameter of the head, varies, the front portion band 120 may be respectively supported on both sides of the object.

The slide band 121 is a slide member capable of moving the front portion band 120 according to an operation position of the object. As an example, the slide band 121 may be provided in a band shape extending in one direction between the crown support unit 112 and the front portion band 120, for example, extending from the crown of the object to the front portion band 120. At this time, a width D2 of the slide band 121 may be 1 cm or more and 10 cm or less, thereby allowing the temporal portion of the object to be opened. Also, at this time, one end of the slide band 121 may be arranged to be fixed to the center of the front portion band 120, and the other end may be supported to be slidable in the front portion case 12, more specifically, the occipital portion support unit 110. As an example, the occipital portion case 12, for example, the occipital portion support unit 110, may be provided with a slide guide on which the slide band 121 may slide. Accordingly, the slide band 121 may be inserted into the occipital portion support unit 110 by sliding in a first direction toward the crown support unit 112 in a first operation mode, for example, when an operation is performed on a frontal lobe, and may be disposed on a front surface of the object by sliding away from the crown support unit 112 in a second direction opposite to the first direction in a second operation mode, for example, when an operation is performed on a temporal lobe. At this time, a slide lock device 114 disposed in the occipital portion support unit 110 may control a slide of the slide band 121 such that a position of the slide band 121 is fixed in each of the first operation mode and the second operation mode. A slide of the front portion case 12 in the first and second operation modes will be described in more detail with reference to FIGS. 4A and 4B.

The temporal portion support units 123 are support members which may be disposed at both ends of the front portion band 120 and supported by the front portion band 120. As an example, the temporal portion support units 123 may be implemented in the form of a pad, which is a protecting and buffering member for improving the wearing convenience of the object. At this time, the temporal portion support units 123 may be disposed inside the front portion band 120, that is, between the temporal portion of the object and the front portion band 120, and thus may be directly supported on the temporal portion of the object.

The first lower face support unit 13 is a support member for supporting a lower face of the object, and may have a band shape extending in one direction. As an example, the first lower face support unit 13 may be arranged such that the respective ends of the first lower face support unit 13 are fixed at both ends of the rear portion case 11. For example, when the object wears the headgear 10, the first lower face support unit 13 may be fixed between the mouth and the jaw of the object to support the lower face of the object. Also, a length of the first lower face support unit 13 may be adjusted according to the head size of the object.

The second lower face support unit 14 is a support member for supporting the lower face of the object, and may have a band shape extending in one direction. As an example, the second lower face support unit 14 may be arranged such that the respective ends of the second lower face support unit 14 are fixed at both ends of the front portion band 120. For example, when the object wears the headgear 10, the second lower face support unit 14 may be fixed between the jaw of the object and the first lower face support unit 13 to support the lower face of the object. Also, a length of the second lower face support unit 14 may also be adjusted according to the head size of the object.

The ultrasound transducer 30 according to an embodiment of the present disclosure may include an ultrasound generating device 31, an applicator 32 and a second marker 33 for identifying a position of the ultrasound transducer 30. The ultrasound generating device 31 according to an embodiment may generate low intensity ultrasound. The low intensity ultrasound may use intensive ultrasound or non-intensive ultrasound. As an example, when the low intensity ultrasound generated by the ultrasound generating device 31 is projected in a specific area, fine mechanical movement may be caused in the specific area of the brain, and thus, brain function may be adjusted. That is, the low intensity ultrasound may be pulsed, and the resulting mechanical energy may be concentrated and synchronized in the specific area of the brain, resulting in a slight vibration. The mechanical vibration generated by the low intensity ultrasound and a transferring motion thereof may enable a receptor of neuronal cells to regulate ion channels to activate or deactivate the brain function.

The applicator 32 may be in a cylindrical shape having one side open, and the ultrasound generating device 31 may be provided on an outer periphery of an opening to be fixed to the scalp of the object. At this time, the applicator 32 may include a bag (not shown) in which water from which gas is removed is filled in a vacuum state such that a space is not generated between the ultrasound generating device 31 and the scalp of the object. At this time, the bag (not shown) may include a flexible synthetic resin material, and the bag (not shown) may be disposed such that the applicator 32 closely contacts a curvature of the scalp of the object without a space.

The second marker 33 is a position sensing unit arranged to determine a position of ultrasound in real time when capturing an MRI image or a CT image. As an example, the second marker 33 may include one or more round bar-shaped infrared reflectors 330 that track a focus direction of the ultrasound generating device 31. As an example, the infrared reflectors 330 may be implemented in four and disposed at four ends of a cruciform support unit, respectively.

The connecting device 40 according to an embodiment of the present disclosure is a connecting member for connecting the ultrasound transducer 30 to the headgear 10. As an example, the connecting device 40 may include a plurality of link structures. At this time, the connecting device 40 may connect first and second connecting bars 45 and 46 using, for example, first through third joints 41 through 43. As an example, the first joint 41 may be arranged to connect the rear portion case 11 provided on the headgear 10 to the first connecting bar 45, and accordingly, one end of the first connecting bar 45 may be moved without any constraint on a three-dimensional space. Also, the second joint 42 may be arranged to connect the first connecting bar 45 to the second connecting bar 46, and accordingly, one end of the second connecting bar 46 may be moved without any constraint on one plane. Also, the third joint 43 may be arranged to connect the second connecting bar 46 to the ultrasound transducer 30. The ultrasound transducer 30 may be disposed in the entire region of the head of the object having the curvature by connecting the rear portion case 11 to the ultrasound transducer 30, using a plurality of joints, and an operation part may be moved and the operation may progress while being supported by the medical headgear 1 worn by the object, thereby improving the operation convenience of the operator. As an example, a link restraining device 47 may be disposed in the second joint 42 to which the first connecting bar 45 and the second connecting bar 46 are connected. Therefore, when the ultrasound transducer 30 is disposed at an operation position of the head of the object, the operator may restrain the first through third joints 41 through 43 using the link restraining device 47, and accordingly, a relative position of the ultrasound transducer 30 relative to the medical headgear 1 may be fixed.

Figure 4A:
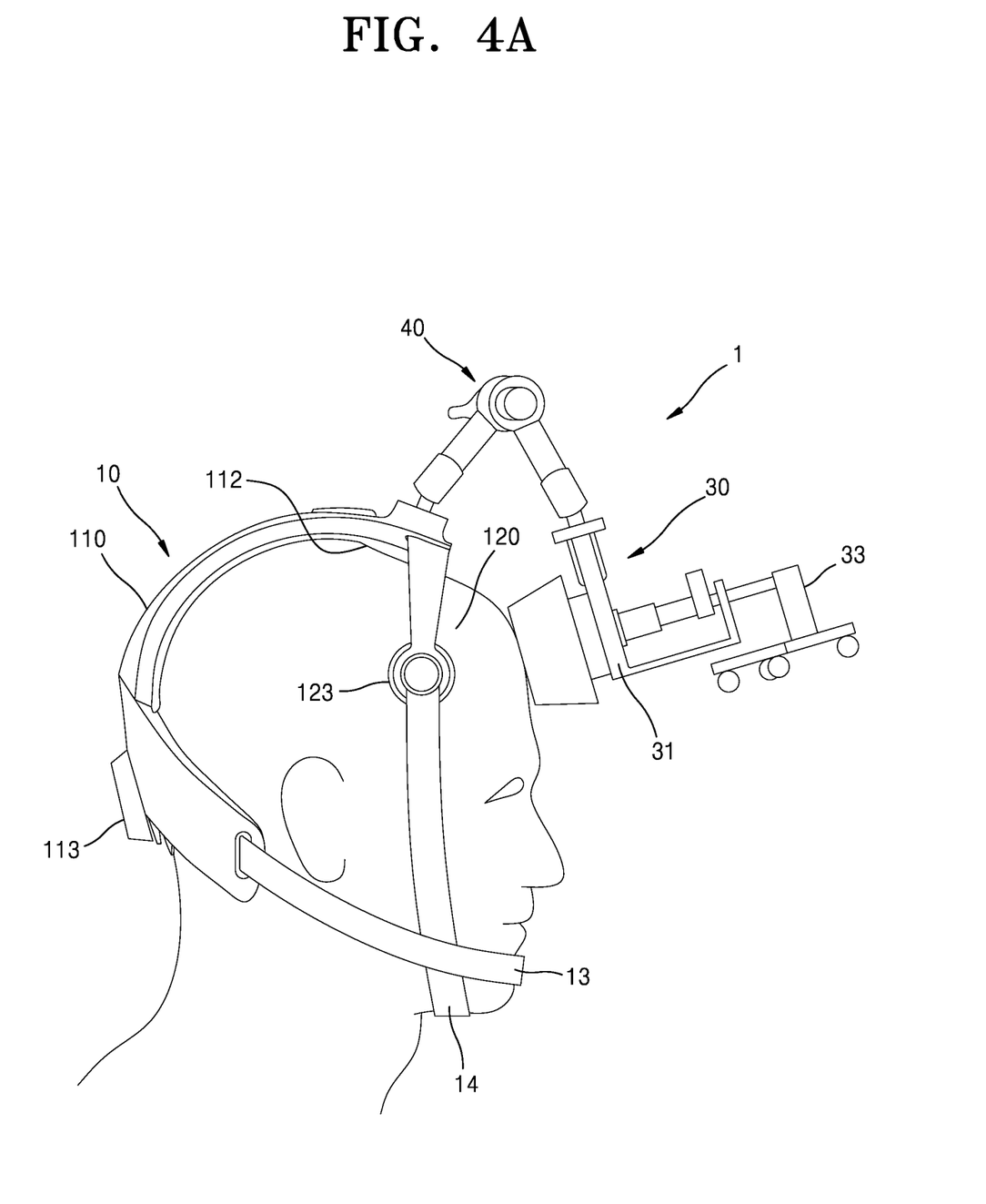
FIGS. 4A and 4B are a side view and a front view, respectively, of an object wearing a medical headgear for a frontal lobe operation according to an embodiment of the present disclosure.
Figure 4B:
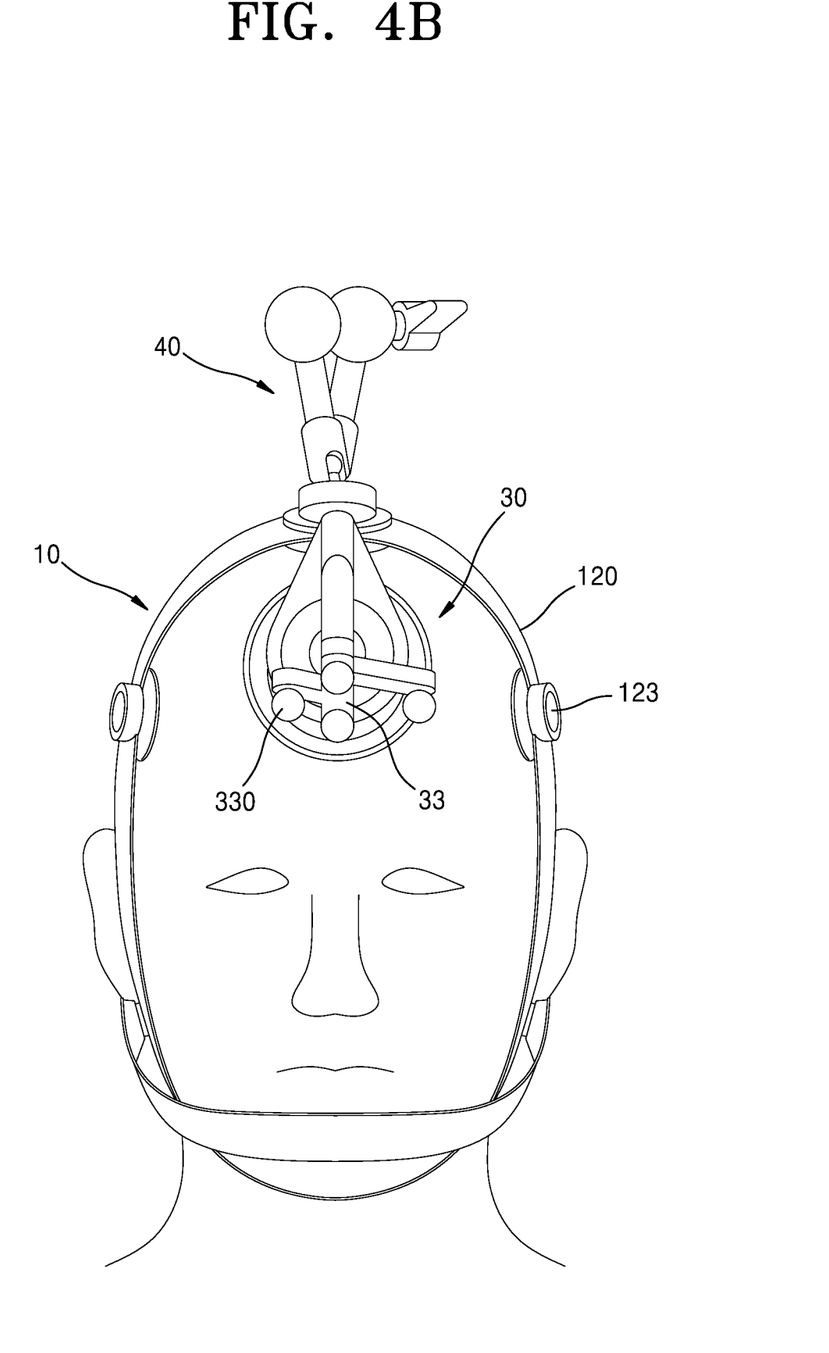

FIGS. 4A and 4B are a side view and a front view, respectively, of an object wearing a medical headgear for a frontal lobe operation according to an embodiment of the present disclosure.

Referring to FIGS. 4A and 4B, according to an embodiment of the present disclosure, the medical headgear 1 may be worn by the object for a first procedure mode, that is, for the frontal lobe operation of the object. As an example, the object may wear the headgear 10. At this time, an occipital and a crown of the object may be supported by the occipital portion support unit 110 and the crown support unit 112. Also, at this time, by adjusting the length of the occipital portion support unit 110 by using the occipital portion regulating unit 113, the head of the object may be tightened or relaxed, and accordingly, the headgear 10 may be worn on the object having various head sizes. Also, at this time, the first lower face support unit 13 and the second lower face support unit 14 may be supported on the lower face of the operator. Also, at this time, the first marker 115 fixed to the occipital portion support unit 110 may sense a position and an orientation of the head of the object wearing the headgear 10 in real time.

Also, as an example, in a first operation mode, the slide band 121 provided in the front portion case 12 may be inserted into the occipital portion support unit 110 by sliding in a first direction toward the crown support unit 112. Accordingly, a frontal lobe of the object may be open and the operator may manipulate the connecting device 40 to dispose the ultrasound transducer 30 on the frontal lobe of the object and then closely adhere and support the ultrasound transducer 30 to the frontal lobe of the object. At this time, a pair of temporal portion support units 123 supported by the front portion band 120 may be respectively supported on a temporal portion of the object. Also, at this time, the second marker 33 fixed to the ultrasound generator 31 may track a focal direction of the ultrasound generator 31 using the round bar-shaped infrared reflector 330.

Figure 5A:
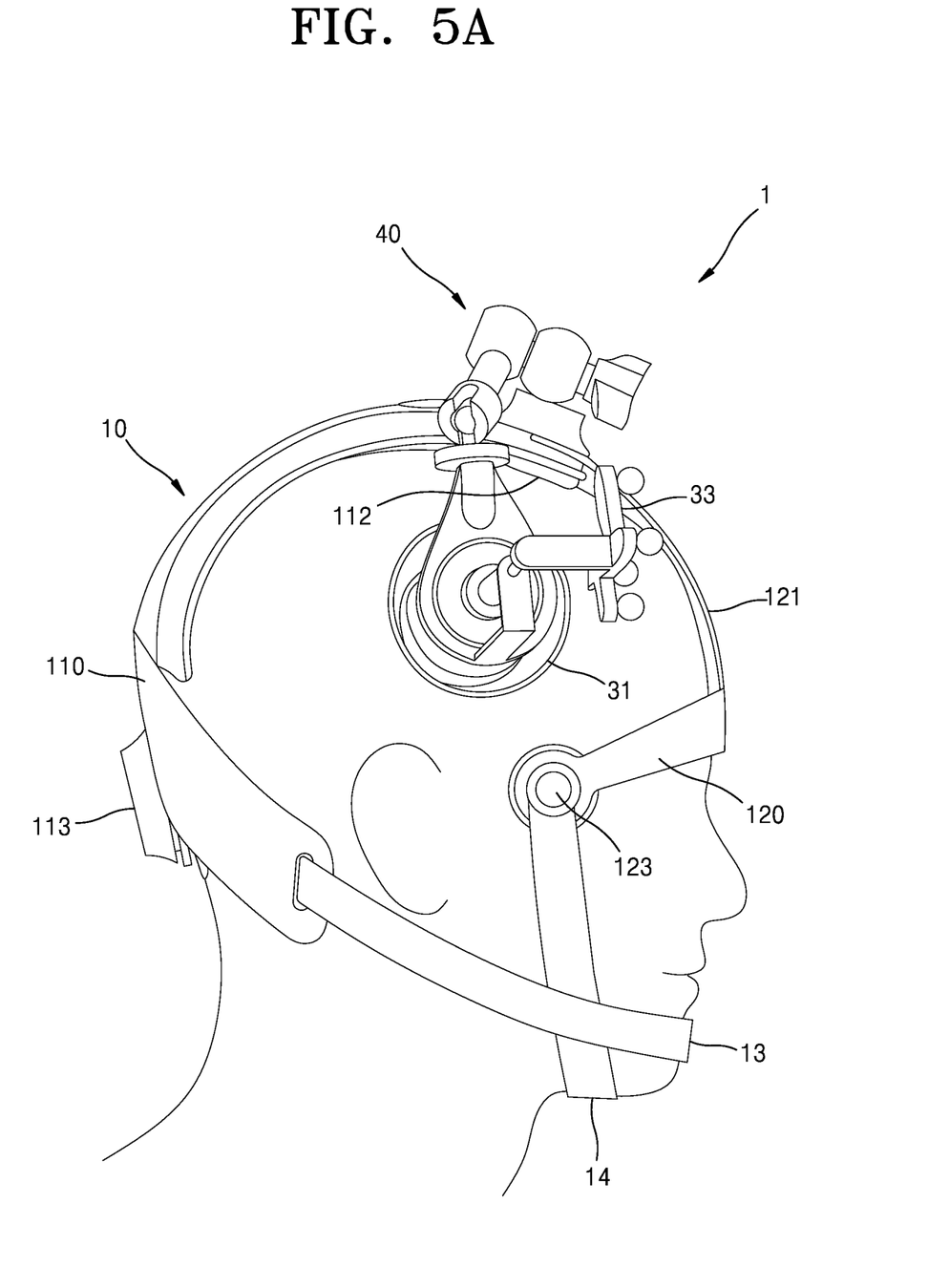
FIGS. 5A and 5B are a side view and a front view, respectively, of an object wearing a medical headgear for a frontal lobe operation according to an embodiment of the present disclosure.
Figure 5B:
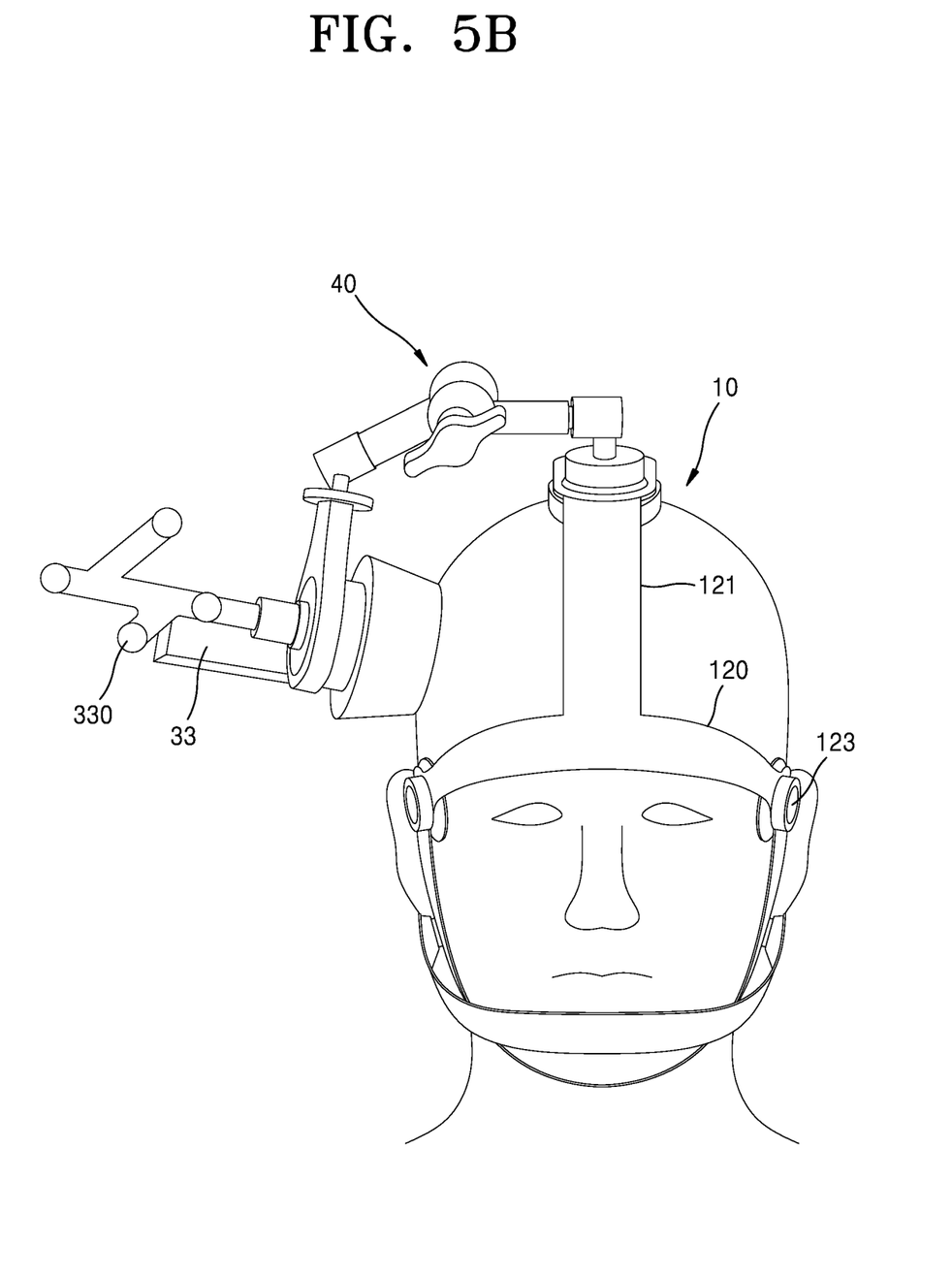

FIGS. 5A and 5B are a side view and a front view, respectively, of an object wearing a medical headgear for a frontal lobe operation according to an embodiment of the present disclosure. For the convenience of description, descriptions that are substantially the same as those given with reference to FIGS. 4A to 4B are omitted.

Referring to FIGS. 5A and 5B, according to an embodiment of the present disclosure, the medical headgear 1 may be worn by the object for a second operation mode, that is, for the temporal lobe operation of the object. As an example, the object may wear the headgear 10. At this time, an occipital and a crown of the object may be supported by the occipital portion support unit 110 and the crown support unit 112. Also, as an example, in the second operation mode, the slide band 121 provided in the occipital portion case 12 may slide so as to be spaced apart from the crown support unit 112 in a second direction opposite to a first direction and discharged from the occipital portion support unit 110. Accordingly, a temporal lobe of the object may be open and the operator may manipulate the connecting device 40 to dispose the ultrasound transducer 30 on the temporal lobe of the object and then closely adhere and support the ultrasound transducer 30 to the temporal lobe of the object. At this time, a pair of temporal portion support units 123 supported by the front portion band 120 may be respectively supported on a temporal portion of the object. At this time, a position of the temporal portion of the object supported by the pair of temporal portion support units 123 may be different from a position of the temporal portion of the object supported by the pair of temporal portion support units 123 shown in FIGS. 4A to 4B. Even when an operation position of the object is different as in the above-described embodiment, the operation may be carried out only by a slide movement of the occipital portion case 12 and a movement of the ultrasound transducer 30, and thus, the use convenience of the operator may be improved.

It will be understood by those skilled in the art that the foregoing description of the present disclosure is for illustrative purposes only and that those of ordinary skill in the art can readily understand that various changes and modifications may be made without departing from the spirit or essential characteristics of the present disclosure. It is therefore to be understood that the above-described embodiments are illustrative in all aspects and not restrictive. For example, each component described as a single entity may be distributed and implemented, and components described as being distributed may also be implemented in a combined form.

The scope of the present disclosure is defined by the appended claims rather than the detailed description and all changes or modifications derived from the meaning and scope of the claims and their equivalents are to be construed as being included within the scope of the present disclosure.

We claim:

1. A medical headgear comprising:
an ultrasound transducer configured to generate a low intensity ultrasound; and
a headgear by which the ultrasound transducer is supported, wherein the headgear comprises:
a rear portion case disposed at a rear portion and configured to support a head of an object, the rear portion case comprising:
an occipital portion support unit configured to support an occipital portion of the head of the object,
an occipital portion pad disposed to face the occipital portion support unit, and
a crown support pad configured to support a crown of the head of the object and is connected to the occipital portion support unit via the occipital portion pad; and
a front portion case connected to the rear portion case to be slidably movable in one direction, the front portion case comprising:
two temporal support pads spaced apart from each other and configured to support both temporal portions of the head of the object,
a front portion band extending between the two temporal support pads, and
a slide band extending between the crown support pad and the front portion band and having a width that allows the temporal portions of the head of the object to be accessible by the ultrasound transducer,
wherein in a first operation mode in which an operation is performed to target toward a frontal lobe;
the slide band slides in a first direction toward the crown support pad by inserting the slide band into the occipital portion support unit and spacing the front portion band apart from a front portion of the head of the object corresponding to the frontal lobe, and
in a second operation mode in which an operation is performed to target toward a temporal lobe;
the slide band slides so as to be spaced apart from the crown support pad in a second direction opposite to the first direction, the slide band and the front portion band configured to engage the front portion of the head of the object corresponding to the frontal lobe in the second operation mode.

2. The medical headgear of claim 1, wherein the front portion band extends between the two temporal support pads disposed at both ends thereof.

3. The medical headgear of claim 2, wherein one end of the slide band is fixed to the front portion band and another end is slidably supported on the rear portion case.

4. The medical headgear of claim 2, wherein the front portion band is provided with an elastic member deformable along a head circumference of the object.

5. The medical headgear of claim 1, further comprising a slide lock configured to fix a position of the slide band according to the first and the second operation modes.

6. The medical headgear of claim 1, further comprising a first marker supported by the rear portion case and configured to sense a position of the medical headgear, the first marker comprising at least one infrared reflector.

7. The medical headgear of claim 1, further comprising a first lower face support unit having two ends supported on two ends of the rear portion case respectively to support a lower face of the object.

8. The medical headgear of claim 1, further comprising a second lower face support unit having two ends supported on two ends of the front portion band respectively to support a lower face of the object.

9. The medical headgear of claim 1, wherein the ultrasound transducer comprises an ultrasound generating device configured to generate the low intensity ultrasound and an applicator configured to fix the ultrasound generating device to a scalp of the object.

10. The medical headgear of claim 9, further comprising a marker supported by the ultrasound transducer and configured to sense a focal direction of the ultrasound generating device, the marker comprising one or more infrared reflectors.

11. The medical headgear of claim 1, further comprising a link structure disposed between the headgear and the ultrasound transducer to connect the headgear to the ultrasound transducer.

12. The medical headgear of claim 11, wherein the link structure comprises a plurality of connecting bars.

13. The medical headgear of claim 12, wherein the link structure comprises a first connecting bar and a second connecting bar disposed between the headgear and the ultrasound transducer, a first joint configured to connect the headgear to the first connecting bar, a second joint configured to connect the first connecting bar to the second connecting bar, and a third joint configured to connect the second joint to the ultrasound transducer.

14. The medical headgear of claim 13, further comprising a link restraining device disposed in the second joint to restrain the first joint to the third joint.

15. The medical headgear of claim 1, wherein a slide guide extends in a circumferential direction of the occipital portion, and further comprises an adjustable dial extending or contracting the slide guide.

16. A transcranial ultrasound transmission device comprising:
the medical headgear of claim 1.

* * * * *